(12) United States Patent
Muto et al.

(10) Patent No.: US 10,687,701 B2
(45) Date of Patent: Jun. 23, 2020

(54) EYEGROUND IMAGING APPARATUS AND CONTROL METHOD THEREFOR

(71) Applicant: CANON KABUSHIKI KAISHA, Tokyo (JP)

(72) Inventors: Kenji Muto, Fujisawa (JP); Yasuyuki Numajiri, Kawasaki (JP); Nobuhito Suehira, Tokyo (JP); Makoto Sato, Tokyo (JP); Yukio Sakagawa, Tokyo (JP); Akihiro Katayama, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 29 days.

(21) Appl. No.: 15/089,104

(22) Filed: Apr. 1, 2016

(65) Prior Publication Data

US 2016/0213246 A1    Jul. 28, 2016

Related U.S. Application Data

(63) Continuation of application No. 13/378,341, filed as application No. PCT/JP2010/004054 on Jun. 17, 2010, now Pat. No. 9,326,678.

(30) Foreign Application Priority Data

Jun. 25, 2009  (JP) .................................. 2009-151485

(51) Int. Cl.
  *A61B 3/14*   (2006.01)
  *A61B 3/10*   (2006.01)
  *A61B 3/12*   (2006.01)
  *A61B 3/00*   (2006.01)

(52) U.S. Cl.
  CPC ............ *A61B 3/102* (2013.01); *A61B 3/0058* (2013.01); *A61B 3/12* (2013.01)

(58) Field of Classification Search
  CPC .. A61B 3/102; A61B 3/14; A61B 3/12; A61B 3/0025; A61B 3/0058;
  (Continued)

(56) References Cited

U.S. PATENT DOCUMENTS 5,943,116 A    8/1999  Zeimer
6,155,683 A  * 12/2000  Hanaki .................. A61B 3/145
                                                351/206

(Continued)

FOREIGN PATENT DOCUMENTS

EP    1836953 A1    9/2007
EP    1908399 A1    4/2008
(Continued)

OTHER PUBLICATIONS

Makoto Kanno; "The List of Instruments of Test for Glaucoma and Models of Optical Coherence Tomography;" May 31, 2008; Journal of the Eye, vol. 25, the May number, pp. 637-645.

*Primary Examiner* — Mahidere S Sahle
(74) *Attorney, Agent, or Firm* — Canon U.S.A., Inc. IP Division

(57) ABSTRACT

A tomographic-image pickup unit is controlled so as to capture a tomographic image in response to a signal input from a signal input unit. Then, a display unit is controlled so as to display the captured tomographic image. An eyeground-image pickup unit is controlled so as to capture a two-dimensional image in response to a signal input from the signal input unit while the tomographic image is displayed on the display unit. Therewith, the user can more easily perform imaging, and the time load on the subject is reduced.

48 Claims, 7 Drawing Sheets

(58) Field of Classification Search
CPC ... A61B 3/1225; A61B 3/0033; A61B 5/0066; A61B 5/0073; G01B 9/02091; G01B 9/02048; G01B 9/02089; G01B 2290/65; G06T 2207/30041; G06T 2207/10101; G06T 2207/30168
USPC .......................................................... 351/206
See application file for complete search history.

(56) References Cited

U.S. PATENT DOCUMENTS

| | | | | |
|---|---|---|---|---|
| 6,396,053 | B1* | 5/2002 | Yokoi | G02B 21/16 250/226 |
| 6,454,410 | B1* | 9/2002 | Berger | A61B 3/0041 351/206 |
| 2007/0291277 | A1* | 12/2007 | Everett | A61B 3/102 356/497 |
| 2008/0068560 | A1* | 3/2008 | Knighton | A61B 3/102 351/206 |
| 2009/0263115 | A1* | 10/2009 | Suzuki | A61B 3/12 396/18 |
| 2010/0201832 | A1* | 8/2010 | Chen | G06K 9/036 348/222.1 |

FOREIGN PATENT DOCUMENTS

| | | |
|---|---|---|
| JP | 2006-126899 A | 5/2006 |
| JP | 2008-175698 A | 7/2008 |
| JP | 2008-209166 A | 9/2008 |
| JP | 2008-267891 A | 11/2008 |
| JP | 2009-042197 A | 2/2009 |
| JP | 2009-066015 A | 4/2009 |

* cited by examiner

EYEGROUND IMAGING APPARATUS AND CONTROL METHOD THEREFOR

CROSS-REFERENCE TO RELATED APPLICATIONS

This application is a Continuation of co-pending U.S. patent application Ser. No. 13/378,341, filed Dec. 14, 2011, which is a U.S. national stage application of International Patent Application No. PCT/JP2010/004054, filed Jun. 17, 2010, which claims the priority benefit of Japanese Patent Application No. 2009-151485, filed Jun. 25, 2009. All of the above-named patent applications are hereby incorporated by reference herein in their entirety.

TECHNICAL FIELD

The present invention relates to an eyeground imaging apparatus and a control method therefor, and more particularly, to an eyeground imaging apparatus used to acquire a surface image and a tomographic image of an eyeground of an eye to be examined, and a control method therefor.

BACKGROUND ART

In recent years, imaging apparatuses using optical coherence tomography (OCT) that utilizes interference of low coherent light (hereinafter also referred to as OCT apparatuses) have been put into practical use. Since an OCT apparatus can acquire a tomographic image only with a resolution substantially equivalent to the wavelength of light incident on an object to be examined, a tomographic image of a sample can be obtained with a high resolution. Particularly in the ophthalmologic field, the OCT apparatus is useful for obtaining a tomographic image of a retina at the eyeground.

A composite apparatus using an OCT apparatus and a retinal camera (an apparatus for capturing a surface image or a two-dimensional image of the eyeground) in combination is also useful. As such a composite apparatus, Japanese Patent Laid-Open No. 2007-252693 discloses an apparatus capable of simultaneously capturing a surface image and a tomographic image of the eyeground. In this composite apparatus, an OCT apparatus is connected to an optical connector of a retinal camera. When a control button of a joystick provided in the retinal camera is pressed, a surface image and a tomographic image of the eyeground are captured simultaneously.

The time taken to capture multiple tomographic images with the OCT apparatus is longer than the time taken to capture surface images of the eyeground with the retinal camera, and often becomes about several seconds. When a tomographic image is captured with the OCT apparatus, the brightness of an acquired tomographic image is low or the positions of a plurality of tomographic images are misaligned because of a blink or involuntary eye movement (the eye of a subject to be examined randomly and slightly moves against the subject's intention not to move the eye) of the subject. As a result, a desired area that is important in diagnosing the retina and optic disk of the eyeground may not be included in the acquired image. In this case, there is a need to capture a tomographic image of the eyeground of the subject again.

In the apparatus disclosed in Japanese Patent Laid-Open No. 2007-252693, when the control button of the joystick provided in the retinal camera is pressed, a tomographic image is first captured, and a surface image of the eyeground is subsequently captured. Thus, a tomographic image and a surface image are captured in succession in this order by one press of the control button. In this case, the surface image of the eyeground is captured before the operator checks the tomographic image.

In contrast, to obtain an image of the eyeground with the retinal camera, it is necessary to illuminate the eyeground with a flare of flashlight. Since the quantity of illumination light is large, the pupil of the subject contracts after a surface image of the eyeground is captured. In this case, according to the subject, it takes several minutes until the pupil dilates. For this reason, the next tomographic image can be captured only when several minutes pass after the surface image of the eyeground is captured.

For the above-described reason, the user of the apparatus needs to wait for a long period to capture a tomographic image again after a surface image of the eyeground is captured, and this reduces usability. Moreover, the subject whose eyeground is to be imaged has a heavy time load.

CITATION LIST

Patent Literature

[PTL 1]
Japanese Patent Laid-Open No. 2007-252693

SUMMARY OF INVENTION

An eyeground imaging apparatus according to an aspect of the present invention includes an eyeground-image pickup unit configured to capture a two-dimensional image of a surface of an eyeground of a subject; a tomographic-image pickup unit configured to capture a tomographic image of the eyeground, the tomographic-image pickup unit having an optical system common to the eyeground-image pickup unit; an output unit configured to output a signal relating to the tomographic image so as to display the tomographic image on a display unit; a control unit configured to exert control over the eyeground-image pickup unit, the tomographic-image pickup unit, and the output unit; and a signal input unit configured to input a signal relating to the control to the control unit. The control unit controls the tomographic-image pickup unit so as to capture the tomographic image in response to a signal input from the signal input unit, controls the output unit so as to output the signal relating to the captured tomographic image to the display unit, and controls the eyeground-image pickup unit so as to capture the two-dimensional image in response to a signal input from the signal input unit when the signal relating to the tomographic image is output from the output unit.

An imaging method for an eyeground imaging apparatus according to another aspect of the present invention includes the steps of capturing a tomographic image of an eyeground of a subject; outputting a signal relating to the tomographic image so as to display the tomographic image on a display unit; selecting an operation of capturing a two-dimensional image of a surface of the eyeground or an operation of retaking a tomographic image when the signal relating to the tomographic image is output; and carrying out the selected operation.

An eyeground imaging apparatus according to a further aspect of the present invention includes an eyeground-image pickup unit configured to capture a two-dimensional image of a surface of an eyeground of a subject; a tomographic-image pickup unit configured to capture a tomographic image of the eyeground, the tomographic-image pickup unit having an optical system common to the eyeground-image pickup unit; an output unit configured to output a signal relating to screen information to be displayed on a display unit; a control unit configured to control the eyeground-image pickup unit, the tomographic-image pickup unit, and the output unit; and a signal input unit configured to input a signal to the control unit. The control unit controls the output unit so as to output a signal for displaying the screen information on the display unit, and exerts control so that one of the eyeground-image pickup unit and the tomographic-image pickup unit operates, on the basis of a kind of the screen information output from the output unit in response to the signal input from the signal input unit.

The screen information may include an adjustment screen for adjusting the two-dimensional image and the tomographic image. The control unit may control the eyeground-image pickup unit when the screen information for displaying the tomographic image is output from the output unit and a signal is input from the signal input unit.

The control unit may control the tomographic-image pickup unit when the screen information for displaying the adjustment image is output from the output unit and a signal is input from the signal input unit.

A control method according to a further aspect of the present invention is provided for an eyeground imaging apparatus including an eyeground-image pickup unit configured to capture a two-dimensional image of a surface of an eyeground of a subject, a tomographic-image pickup unit configured to capture a tomographic image of the eyeground, the tomographic-image pickup unit having an optical system common to the eyeground-image pickup unit, an output unit configured to output a signal relating to screen information to be displayed on a display unit, a control unit configured to control the eyeground-image pickup unit, the tomographic-image pickup unit, and the output unit, and a signal input unit configured to input a signal to the control unit. The control method comprises the steps of controlling the output unit so as to output a signal for displaying the screen information on the display unit; and exerting control so that a pickup operation is performed by one of the tomographic-image pickup unit and the eyeground-image pickup unit, on the basis of a kind of the screen information output from the output unit in response to the signal input from the signal input unit.

A control method according to a still further aspect of the present invention is provided for an eyeground imaging apparatus including an eyeground-image pickup unit configured to capture a two-dimensional image of a surface of an eyeground of a subject, a tomographic-image pickup unit configured to capture a tomographic image of the eyeground, the tomographic-image pickup unit having an optical system common to the eyeground-image pickup unit, an output unit configured to output a signal for displaying the tomographic image to a display unit, a control unit configured to control the eyeground-image pickup unit, the tomographic-image pickup unit, and the output unit, and a signal input unit configured to input a signal to the control unit. The control method comprises the steps of controlling the tomographic-image pickup unit so as to capture the tomographic image in response to the signal input from the signal input unit; controlling the output unit so as to output the signal for displaying the captured tomographic image on the display unit; and controlling the eyeground-image pickup unit so as to capture the two-dimensional image when the signal for displaying the tomographic image is output from the output unit and a signal is input from the input unit.

According to the present invention, a surface image of the eyeground can be captured after a tomographic image is checked. Hence, even if there is a need to capture a tomographic image again because of image displacement due to, for example, involuntary eye movement, the tomographic image can be efficiently captured by checking the previous tomographic image. Moreover, the user can more easily capture the image, and the time load on the subject is reduced.

Further features of the present invention will become apparent from the following description of exemplary embodiments with reference to the attached drawings.

DESCRIPTION OF EMBODIMENTS

Figure 1A:
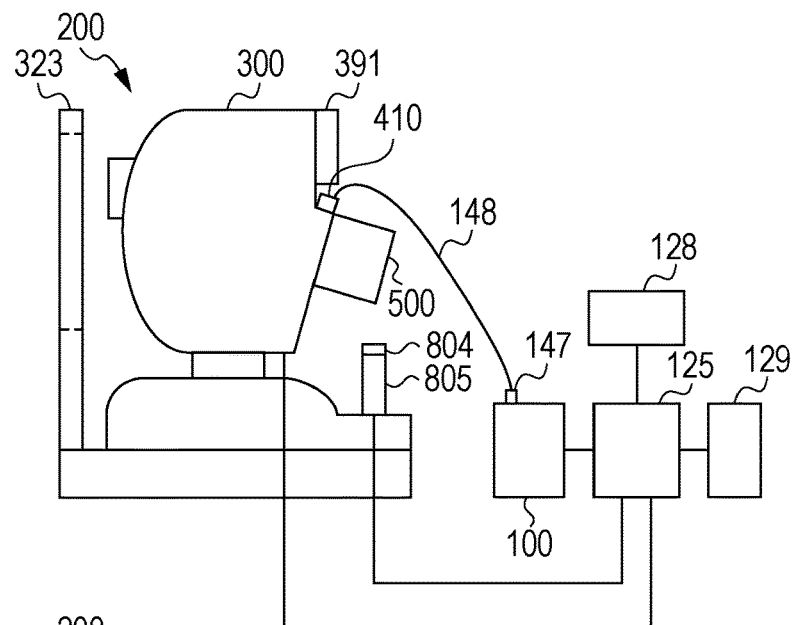
FIG. 1A is a schematic view illustrating an overall configuration of an eyeground imaging apparatus according to first and second examples.

An eyeground imaging apparatus according to an embodiment will be described with reference to FIG. 1A and so on. An eyeground apparatus refers to an apparatus that can capture an image to be used for observation of the eyeground of a subject to be examined. In this case, observation may include observation with the naked eye.

Figure 5A:
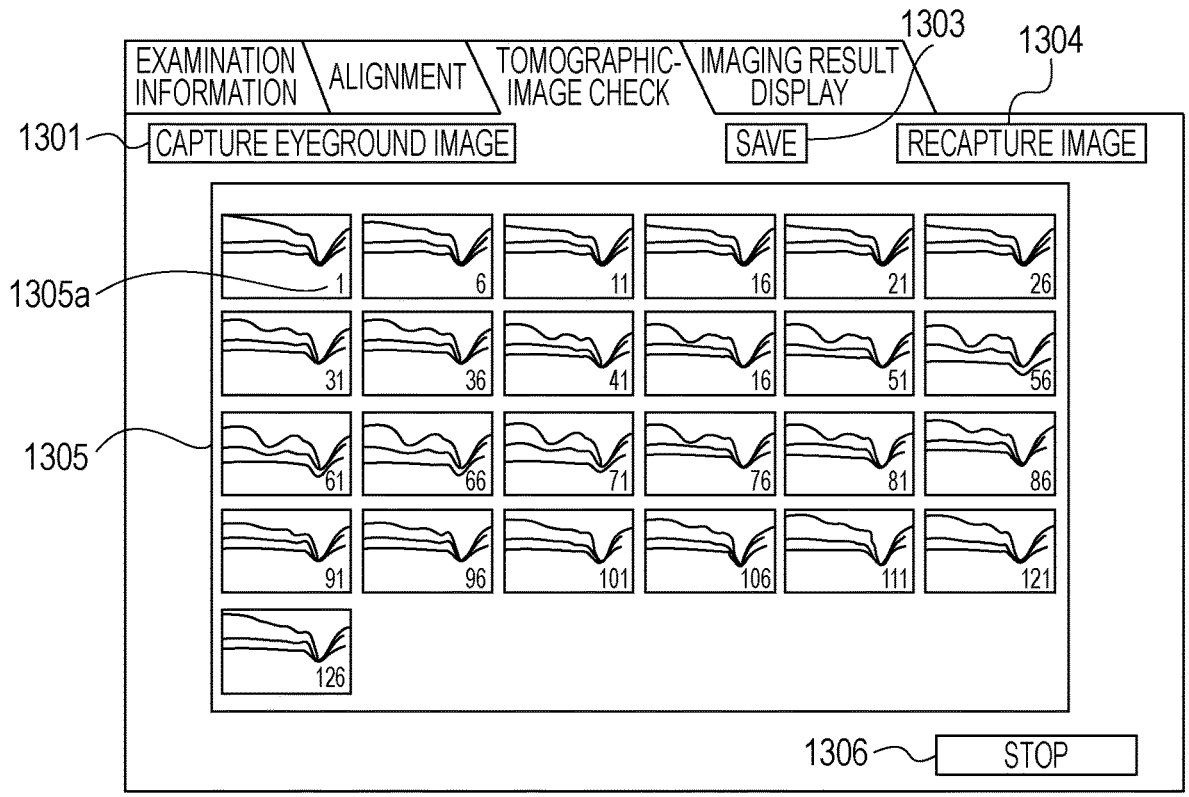
FIG. 5A illustrates a display screen of the first example.
Figure 5B:
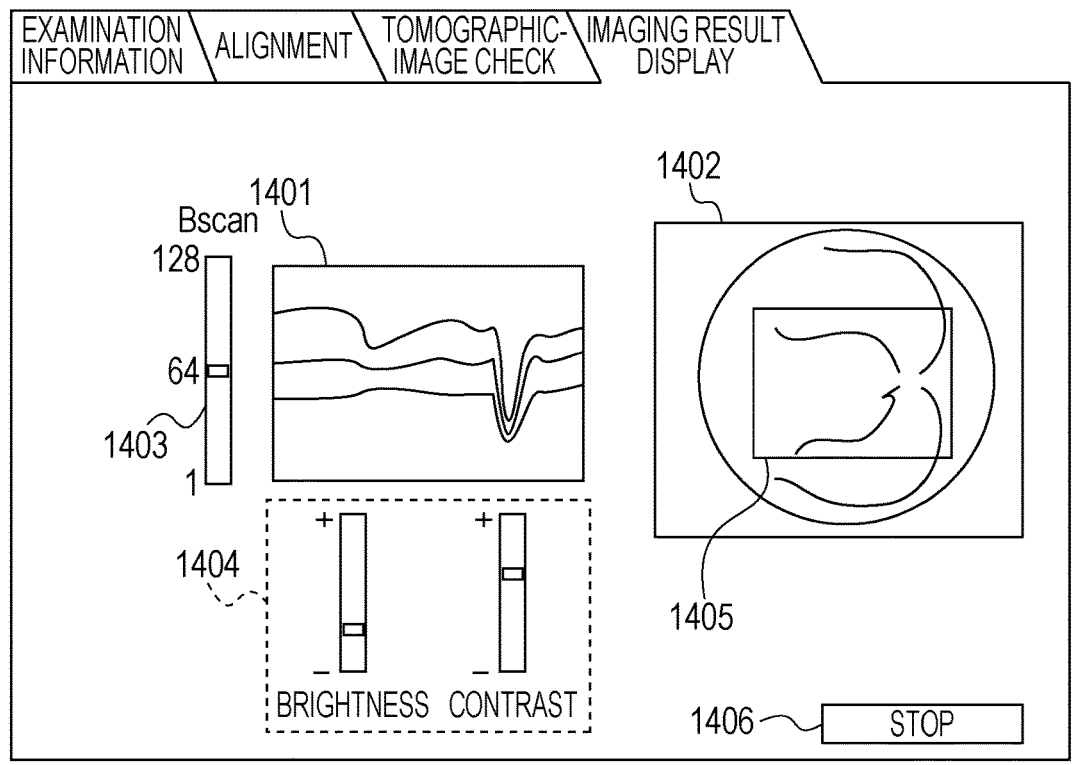
FIG. 5B illustrates a display screen of the first example.

An eyeground imaging apparatus 200 of the embodiment includes an eyeground-image pickup unit (also referred to as a retinal-camera main unit) 300 that can capture a two-dimensional surface image of an eyeground (e.g., an eyeground image 1402 shown in FIG. 5B). Preferably, a camera unit 500 is removably attached to the eyeground-image pickup unit 300.

A tomographic-image pickup unit 100 has an optical system common to the eyeground-image pickup unit 300, and serves to capture a tomographic image of the eyeground (e.g., a B-scan image 1401 shown in FIG. 5B). Preferably, the tomographic-image pickup unit 100 and the eyeground-image pickup unit 300 are optically connected by an optical fiber 148.

A display unit 128 for displaying the tomographic image 1401 is connected via an output unit of the apparatus. The output unit outputs a signal relating to the tomographic image 1401 to the display unit 128, and may be incorporated in a control unit 125 that will be described below or be provided separately from the control unit 125.

The control unit 125 controls the eyeground-image pickup unit 300, the tomographic-image pickup unit 100, and the output unit.

Signals for controlling the eyeground-image pickup unit 300, the tomographic-image pickup unit 100, and the output unit are input to a signal input unit 804. The signal input unit 804 is not limited to a control switch 804 provided in a joystick 805 shown in FIG. 1A, but may be any member capable of inputting signals to the control unit 125, for example, a tomographic-image pickup button 1203 shown in FIG. 4B.

In this case, the control unit 125 performs the following steps (a) to (c):
(a) In response to a signal input from the signal input unit 804 (e.g., a first signal input by the first press of the control switch 804), the control unit 125 controls the tomographic-image pickup unit 100 so as to capture a tomographic image (e.g., a check tomographic image 1305 including a plurality of B-scan images shown in FIG. 5A).
(b) The control unit 125 controls the output unit so as to output a signal relating to the captured tomographic image 1305.
(c) When the signal relating to the tomographic image 1305 is output to the output unit, in response to a signal input from the signal input unit 804 (e.g., a second signal input by the second press of the control switch 804), the control unit 125 controls the eyeground-image pickup unit 300 so as to capture a two-dimensional image 1402.

The above steps allow the eyeground image 1402 to be captured after the tomographic image 1305 is checked. Even when there is a need to capture a tomographic image again because of image misalignment due to involuntary eye movement, the tomographic image can be efficiently captured by checking the previous tomographic image.

It is preferable to provide a selection input unit 1304 (also referred to as a tomographic-image retake button) for selecting retake of a tomographic image 1305. The selection input unit 1304 may be formed by any member capable of inputting a signal to the control unit 125, for example, an alignment tab. Preferably, when a signal relating to a tomographic image 1305 is output from the output unit, the control unit 125 controls the tomographic-image pickup unit 100 so as to capture a tomographic image (retake a check tomographic image 1305) in response to a signal input from the selection input unit 1304. In this case, a tomographic image can be retaken before the pupil of the subject dilates, and therefore, retake can be repeated in a short time.

Preferably, the control unit 125 outputs a signal relating to screen information (e.g., screens shown in FIGS. 4 and 5) from the output unit to the display unit 128 on the basis of a signal input from the signal input unit 804 or the selection input unit 1304.

Figure 4A:
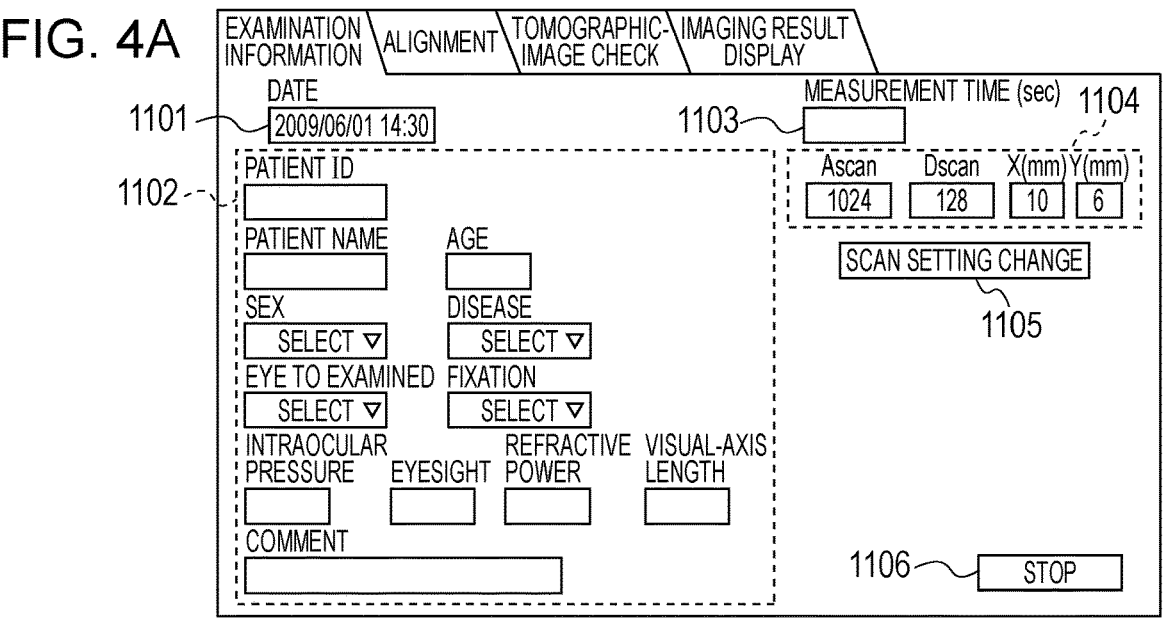
FIG. 4A illustrates a display screen of the first and second examples.
Figure 4B:
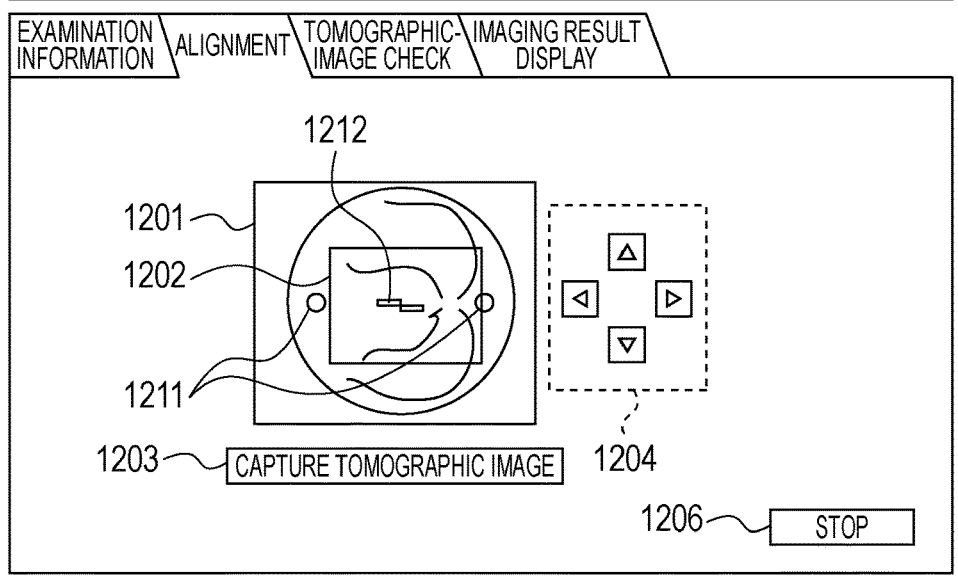
FIG. 4B illustrates a display screen of the first and second examples.
Figure 4C:
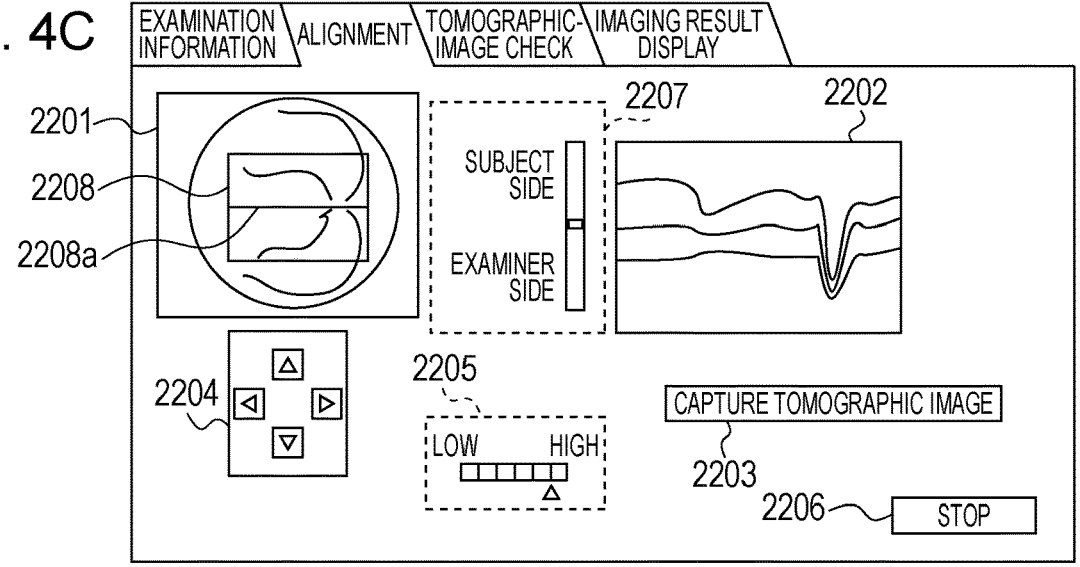
FIG. 4C illustrates a display screen of the first and second examples.

Preferably, the above-described screen information includes an adjustment screen (e.g., screens to be displayed by clicking an alignment tab, as shown in FIGS. 4B and 4C) for adjusting an imaging mode in which a two-dimensional image 1402 or a tomographic image 1401 is captured (e.g., various parameters for imaging, position adjustment). In this case, preferably, the control unit 125 controls the eyeground-image pickup unit 300 or the tomographic-image pickup unit 100 on the basis of a signal relating to the imaging mode adjusted on the adjustment screen.

The first signal in the above-described step (a) may be input by the second press of the control switch 804. In this case, a signal input by the first press is a signal for capturing a tomographic image for a preview, and a signal input by the second press after the preview serves as the first signal. Further, the second signal is a signal input by the third press. These signals will be described in detail in the following description of a second example.

Figure 1B:
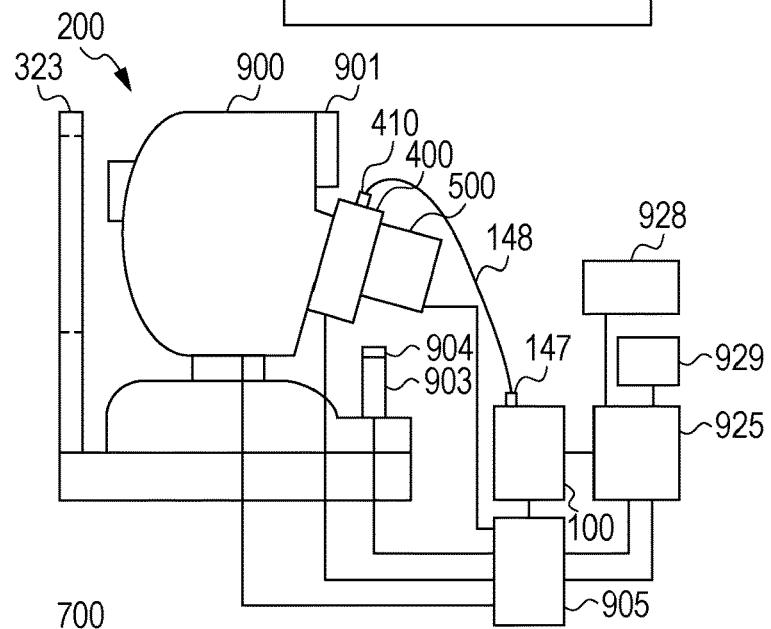
FIG. 1B is a schematic view illustrating an overall configuration of an eyeground imaging apparatus according to a third example.

It is also preferable to provide an adaptor unit 400, as shown in FIG. 1B. In this case, the eyeground-image pickup unit 300 includes a main unit 900 and a camera unit 500 in which a camera is detachably mounted. The adaptor unit 400 is removably provided between the main unit 900 and the camera unit 500, and splits the optical path toward the camera unit 500 and the tomographic-image pickup unit 100. In this case, it is preferable to provide a control circuit unit 905 for inputting a signal input from a signal input unit 904 to the adaptor unit 400 and the main unit 900. These units will be described in detail in the following description of a third example.

While the eyeground imaging apparatus according to the embodiment has been described above, the present invention is not limited to the embodiment.

[Control Method]

Next, a description will be given of a control method for the eyeground imaging apparatus of the embodiment. The control method includes the following steps (a-1) and (b-1):
(a-1) a step of controlling the output unit so as to output a signal for displaying screen information (e.g., screens shown in FIGS. 4 and 5) to the display unit; and
(b-1) a step of exerting control so that one of the tomographic-image pickup unit 100 and the eyeground-image pickup unit 300 performs imaging according to the kind of the screen information output from the output unit (e.g., screens shown in FIGS. 4B and 4C to be displayed by a click of an alignment tab, the screen to be displayed differs according to the tab).

[Imaging Method]

A description will be given of an imaging method adopted in the eyeground imaging apparatus of the embodiment. The imaging method includes the following steps (a-2) to (d-2):
(a-2) a step of capturing a tomographic image of the eyeground of a subject;
(b-2) a step of outputting a signal relating to the tomographic image so as to display the tomographic image on the display unit;
(c-2) a step of capturing a two-dimensional surface image of the eyeground (e.g., clicking an eyeground-image pickup button 1301 shown in FIG. 5A) or retaking a tomographic image (e.g., clicking a tomographic-image retake button 1304 shown in FIG. 5A) when the signal relating to the tomographic image is output; and
(d-2) a step of carrying out the selected image pickup operation.

Therewith, the surface image of the eyeground can be captured after the tomographic image is checked. For this reason, even if there is a need to retake a tomographic image because of image misalignment due to involuntary eye movement, the tomographic image can be efficiently captured by checking the previous tomographic image.

[Storage Medium and Program]

As another embodiment, the imaging method of the above-described embodiment may be stored, as a program to be executed by a computer, in a computer-readable storage medium (e.g., a flexible disk, a hard disk, an optical disc, a magnetooptical disc, a CD-ROM, a CD-R, a magnetic tape, a nonvolatile memory card, a ROM, an EEPROM, or a Blu-ray disc).

EXAMPLES

First Example

Eyeground Imaging Apparatus and Control Method Therefor

First, an overall configuration of an eyeground imaging apparatus according to a first example will be described with reference to FIG. 1A. FIG. 1A is a side view of an eyeground imaging apparatus 200 of the first example. The eyeground imaging apparatus 200 includes a tomographic-image pickup unit 100, a retinal-camera main unit 300, and a camera unit 500. The main unit 300 is optically connected to the camera unit 500, and is also optically connected to the tomographic-image pickup unit 100 by an optical fiber 148. The main unit 300 and the tomographic-image pickup unit 100 have a connector 410 and a connector 147, respectively. A jaw rest 323 fixes the jaw and forehead of the subject so as to fix the eye to be examined. A monitor 391 displays, for example, an infrared image for adjustment during image pickup operation.

A joystick 805 controls movement for aligning the main unit 300 with the eye to be examined, and a control switch 804 serves as a signal input unit for inputting signals for capturing a tomographic image and an eyeground image. A control unit 125 is formed by a personal computer, and controls the main unit 300 and the camera unit 500 and controls the layout of tomographic images and displays of tomographic images and eyeground images. A control-unit monitor 128 serves as a display unit, and a storage unit 129 is formed by a hard disk that stores programs and obtained images. The storage unit 129 may be incorporated in the control unit 125. Here, the camera unit 500 is a general digital single-lens reflex camera, and is connected to the main unit 300 by a general camera mount. [Configuration of Optical System in Main Unit]

Figure 2A:
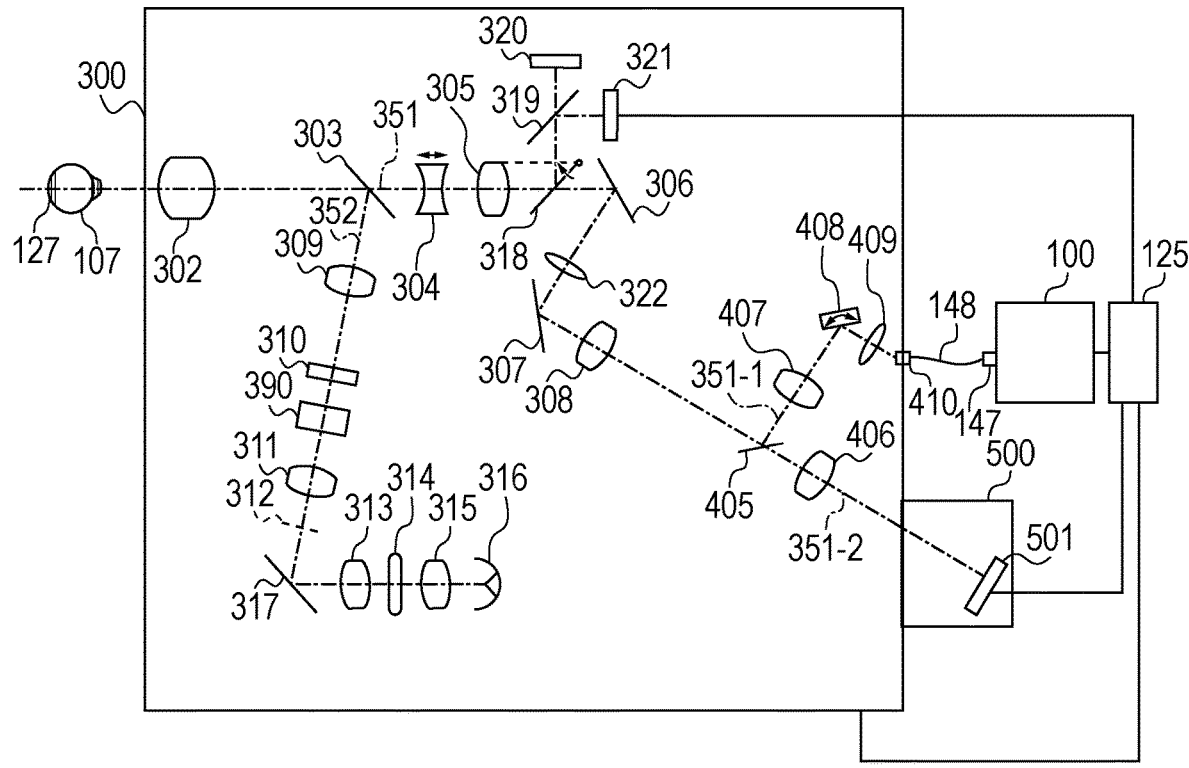
FIG. 2A is a schematic view illustrating a configuration of an optical system of the first example.

A configuration of an optical system in the main unit 300 will be described with reference to FIG. 2A.

The eyeground imaging apparatus 200 obtains a tomographic image (OCT image) and an eyeground image (planar image) of a retina 127 of an eye 107 to be examined with the tomographic-image pickup unit 100 and the camera unit 500.

First, the main unit 300 will be described. An objective lens 302 is provided to oppose the eye 107, and the optical path is split into an optical path 351 and an optical path 352 by a perforated mirror 303.

The optical path 352 forms an illumination optical system for illuminating the eyeground of the eye 107. In a lower part of the eyeground-image pickup unit 300, a condenser lens 313, a stroboscopic tube 314 used to image the eyeground of the eye 107, a condenser lens 315, a halogen lamp 316 used to position the eye 107, and a mirror 317 are provided. Illumination light traveling from the halogen lamp 316 via the stroboscopic tube 314 is shaped into a ring-shaped light beam by a ring slit 312, travels via a lens 311, an alignment optical system 390, an optical filter 310, and a lens 309, is reflected by the perforated mirror 303, and then illuminates the eyeground of the eye 107. The alignment optical system 390 projects a split image used for focusing on the eyeground and an index used to align the eye 107 with the optical axis of the optical system of the main unit 300.

The optical path 351 forms an imaging optical system for capturing a tomographic image and an eyeground image of the eyeground of the eye 107. On the right side of the perforated mirror 303, a focus lens 304 and an imaging lens 305 are provided. Here, the focus lens 304 is supported to be movable in the optical-axis direction with operation of a knob (not shown) by the examiner. The optical path 351 is further guided to a fixation lamp 320 and an infrared area sensor 321 via a quick-return mirror 318. The quick-return mirror 318 transmits infrared light within a wavelength range used to capture a tomographic image, but does not transmit visible light used to capture an eyeground image. Image information acquired by the infrared area sensor 321 is displayed on the display unit 128 or the monitor 391 (see FIG. 1), and is used to position the eye 107. Here, a surface of the quick-return mirror 318 is covered with a silver film and a protective film that are deposited in order. A dichroic mirror 319 is designed to separately guide the visible light toward the fixation lamp 320 and the infrared light toward the infrared area sensor 321. Further, the optical path 351 is guided to the camera unit 500 via a mirror 306, a field lens 322, a mirror 307, and a relay lens 308.

On the other hand, the optical path 351 is split into an optical path 351-1 for pickup of a tomographic image and an optical path 351-2 for pickup of an eyeground image. Here, a relay lens 406 is provided in the optical path 351-2, and a relay lens 407, an XY scanner 408, and a collimating lens 409 are provided in the optical path 351-1. While the XY scanner 408 is shown by one mirror for simplicity, it is, in actuality, formed by adjacent two mirrors, namely, an X-scan mirror and a Y-scan mirror, and performs raster-scanning over the retina 127 in a direction perpendicular to the optical axis. The optical axis of the optical path 351-2 is adjusted in a manner such as to coincide with the rotation centers of the two mirrors in the XY scanner 408. The optical fiber 148 is attached by the connector 410.

The camera unit 500 is a digital single-lens reflex camera for capturing an eyeground image. Since the camera unit 500 is connected to the main unit 300 by a general camera mount, it is easy to attach and detach. An eyeground image is formed on a surface of an area sensor 501.

[Configuration of Tomographic-Image Pickup Unit]

Next, a configuration of the tomographic-image pickup unit 100 will be described with reference to FIG. 2B.

In the first example, the tomographic-image pickup unit 100 obtains a tomographic image of the retina 127 of the eye 107. Further, since a part of the optical system of the tomographic-image pickup unit 100 is formed by an optical fiber, size reduction is achieved. While the optical fiber is adopted in the optical path in the first example, it does not always need to be used.

Figure 2B:
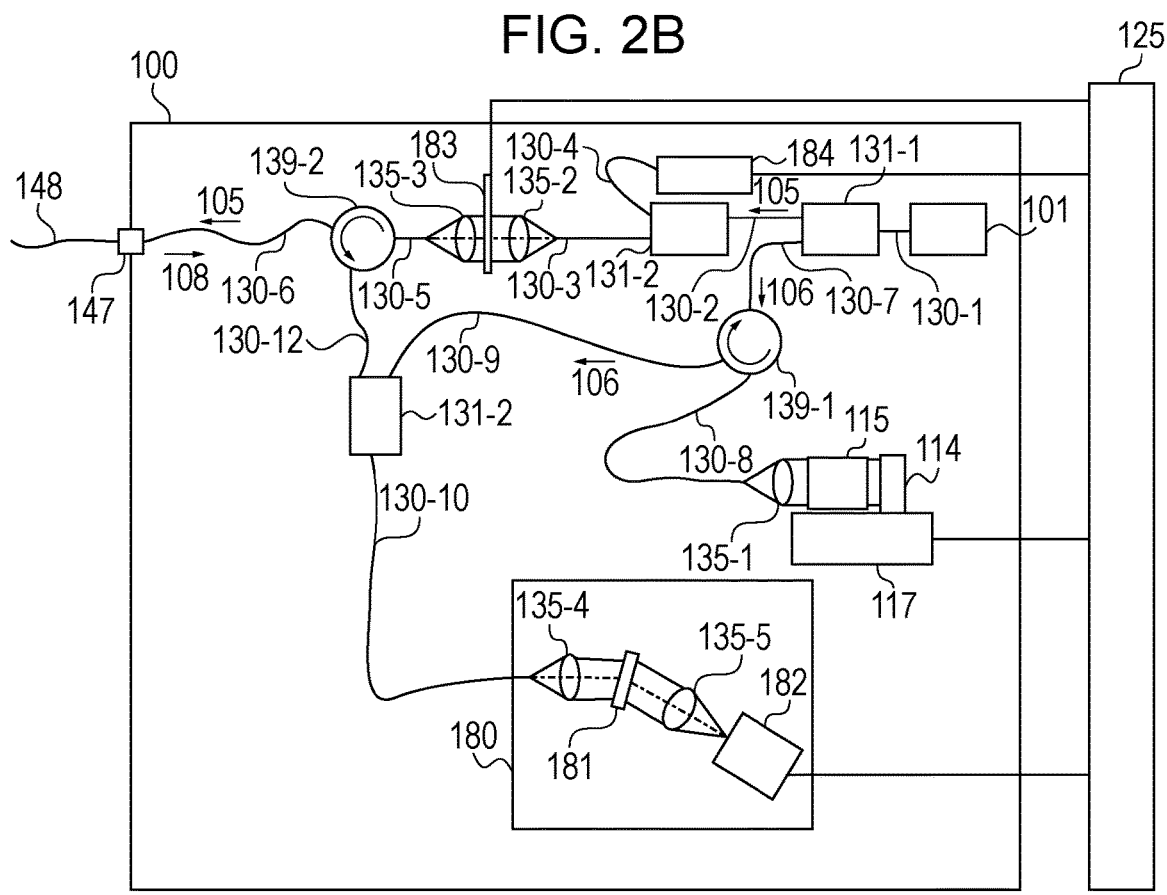
FIG. 2B is a schematic view illustrating the configuration of the optical system of the first example.

With reference to FIG. 2B, the configuration of the tomographic-image pickup unit 100 will be described. The tomographic-image pickup unit 100 forms a Mach-Zehnder interferometer. Light emitted from a light source 101 is split into measurement light 105 and reference light 106 via an optical coupler 131-1. Further, light traveling toward a light detector 184, such as a photodetector, for monitoring the light quantity branches off from the measurement light 105 via an optical coupler 131-2. The measurement light 105 is guided to an optical fiber 130-5 via lenses 135-2 and 135-3. A shutter 183 is provided between the lenses 135-2 and 135-3, and the control unit 125 can determine whether or not to block the light traveling toward the eye 107 with the shutter 183. More specifically, a solenoid (not shown) of the shutter 183 is controlled by the control unit 125 so that a plate-shaped light block member moves into and out of the optical path. Since the measurement light 105 is guided by an optical circulator 139-2 in a direction of arrow shown in the optical circulator 139-2, it is guided by an optical fiber 130-6, and travels toward the main unit 300 via the connector 147.

After that, the measurement light 105 is applied onto the retina 127 of the eye 107 to be examined via the main unit 300, is returned as return light 108 by reflection and scattering of the retina 127. The return light 108 is directed by the optical circulator 139-2 in the direction of the arrow in the optical circulator 139-2, is guided to an optical fiber 130-12, and then reaches an optical coupler 131-2.

In contrast, the reference light 106 travels via an optical circulator 139-1 in a direction of arrow shown in the optical circulator 139-1. Hence, the reference light 106 is guided to an optical fiber 130-8, reaches a mirror 114 via a lens 135-1 and a dispersion-compensating glass 115 inserted to align dispersions of the measurement light and the reference light, and is then reflected by a mirror 114. The reference light 106 reaches the optical circulator 139-1 via the dispersion-compensating glass 115, the lens 135-1, and the optical fiber 130-8, and travels in the direction of the arrow shown in the optical circulator 139-1. Thus, the reference light 106 reaches the optical coupler 131-2 along an optical fiber 130-9.

The optical coupler 131-2 multiplexes the return light 108 and the reference light 106. In the interferometer, when the optical path lengths of the measurement light and the reference light become substantially equal, interference occurs. Accordingly, the mirror 114 is held to be adjustable. After the reference light 106 and the return light 108 are multiplexed, they are guided to a spectroscope 180. In the spectroscope 180, the multiplexed light is collimated by a lens 135-4, is demultiplexed by a diffraction grating 180, and is focused onto a line sensor 182 by a lens 135-5.

Next, the surroundings of the light source 101 will be described. The light source 101 is formed by a super luminescent diode (SLD) serving as a typical low coherent light source, and has a wavelength of 830 nm and a bandwidth of 50 nm. The bandwidth is an important parameter because it has an influence on resolution of an obtained tomographic image in the optical-axis direction. While the SLD is selected as the light source in this example, any light source capable of emitting low coherent light, such as an amplified spontaneous emission (ASE) light source, may be used. In consideration of measurement of the eye, near-infrared light is suitably adopted. Further, it is preferable that the wavelength be as short as possible because the wavelength has an influence on resolution of an obtained tomographic image in the lateral direction, and accordingly, the wavelength is set at 830 nm in the first example. Other wavelengths may be selected according to the portion of the object to be measured. Light emitted from the light source 101 is guided to the optical coupler 131-1 through the optical fiber 130-1.

While the Mach-Zehnder interferometer is used as the interferometer in the first example, it may be replaced with a Michelson interferometer having a simpler structure. In general, it is preferable to use a Mach-Zehnder interferometer when the light quantity difference between the measurement light and the reference light is large, and to use a Michelson interferometer when the light quantity difference is relatively small.

For example, the shutter 183 may be formed of liquid crystal that can control transmission and block of the light, or may be formed by a mirror whose angle is controllable so as to permit or inhibit entry of light into the optical fiber 130-5. [Method for Capturing Tomographic Image and Eyeground Image]

Figure 3:
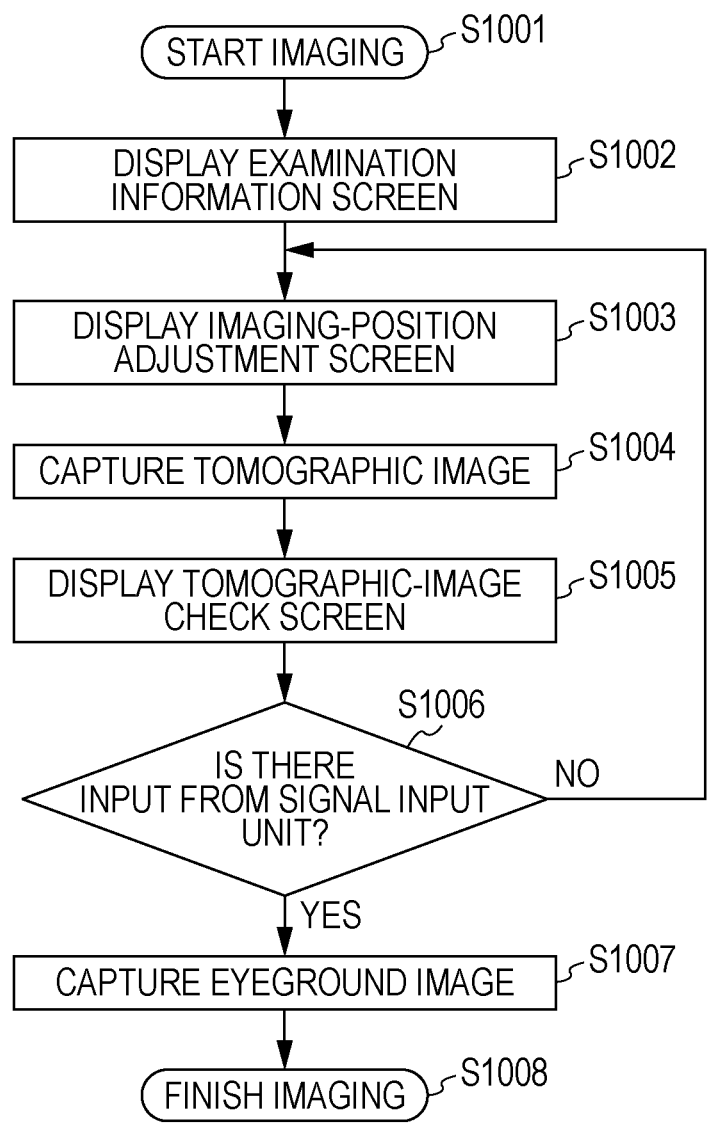
FIG. 3 is a flowchart showing image acquisition in the first example.

Next, a description will be given of a method for capturing a tomographic image and an eyeground image with the eyeground imaging apparatus 200. The eyeground imaging apparatus 200 can obtain a tomographic image of a desired portion of the retina 127 by controlling the XY scanner 408, and obtains en eyeground image after the tomographic image is obtained. The following steps shown in an imaging flowchart of FIG. 3 will be described in order.

In Step S1001, imaging is started. The control unit 125 executes an imaging program, and displays an imaging screen on the control-unit monitor 128.

In Step S1002, an examination information screen (or initial screen) is displayed on the control-unit monitor 128. This display is performed immediately after the imaging screen is displayed. FIG. 4A illustrates the examination information screen.

The date and time are displayed in a portion 1101. Patient information is entered in a portion 1102. A patient ID, patient name, age, intraocular pressure, eyesight, refractive power, and visual axis length can be entered in characters or numerals from an input device (not shown) such as a keyboard. Further, the sex, disease, eye to be examined (left or right), and fixation position (macula, optic disk) can each be selected from a pull-down menu. Since broken lines are shown in FIG. 4A in order to describe the first example, they do not need to be displayed actually.

In a portion 1104, scan settings of the XY scanner 408 for capturing a tomographic image are displayed. The number of image pickup operations to be performed in the x-direction (a direction substantially perpendicular to the depth direction of the eyeground of the subject) is displayed in "Ascan" (a tomographic image to be captured in one pickup operation in the depth direction). Further, the number of image pickup operations to be performed in the y-direction (a direction substantially perpendicular to the depth direction and substantially perpendicular to the x-direction) is displayed in "Bscan" (a two-dimensional tomographic image). Moreover, image pickup areas in the x-direction and y-direction are shown in units of mm.

Scanning of the XY scanner 408 will now be described. First, scanning is performed in the x-direction, and the image pickup area in the x-direction is read a number of times equal to the Ascan number with the line sensor 182. After that, the scanning position in the y-direction is moved, and scanning in the x-direction is performed again. These operations are repeated by scanning the y-direction imaging area a number of times equal to the Bscan number. A portion 1103 indicates an estimated time to be taken for scanning determined by the displayed scan settings. For example, when the reading frequency of the line sensor 182 is 35 kHz, the measurement time displayed in the portion 1103 is given as follows:

$$(1/35000) \times 1024 \times 128 \approx 3.74 \text{ sec} \qquad \text{[Math 1]}$$

To change the displayed scan settings, a scan-setting change button 1105 is clicked to display a special setting screen. A description of the setting screen will be omitted. A stop button 1106 is used to stop imaging.

During Steps S1001 and S1002, the shutter 183 shown in FIG. 2B is in a state such as to block the measurement light. After start-up, the light quantity is constantly monitored by the light detector 184, regardless of the step. When the light quantity exceeds a set value, it is determined that the quantity of light traveling toward the eye increases, and the shutter 183 is kept closed so that the measurement light does not travel toward the eye 107. Moreover, an error message "LIGHT QUANTITY ERROR" is displayed.

In Step S1003, an imaging-position adjustment screen is displayed on the monitor, as shown in FIG. 4B. Switching of the display is made when the examiner clicks an "ALIGNMENT" TAB shown in FIG. 4A. An infrared-image screen 1201 of the eyeground is obtained by superimposing a tomographic-image pickup area 1202 on an image obtained by the infrared area sensor 321 shown in FIG. 2A. More specifically, the infrared-image screen 1201 is shown as a figure indicating the scanning area displayed on the examination information screen shown in FIG. 4A. A button 1204 is used to move the tomographic-image pickup area 1202 up, down, right or left. A tomographic-image pickup button 1203 is a signal input unit for an image pickup signal. A stop button 1206 is similar to the stop button 1106 described in the above description of Step S1002. In this Step S1003, the examiner aligns the eyeground imaging apparatus 200 with the eye 107. More specifically, the examiner places working dots 1211 at symmetrical positions in the up-down direction and right-left direction and minimizes the size of the working dots 1211 by operating the joystick 805 while viewing the infrared-image screen 1201 or the monitor 391 provided in the eyeground-image pickup unit 300. This allows the optical axis of the apparatus to coincide with the optical axis of the eyeground, and forms an appropriate distance between the eye 107 and the objective lens 302. Focus onto the eyeground is adjusted by turning the knob (not shown) to move the lens 305 shown in FIG. 2A so that two splits 1212 are aligned horizontally. This alignment is similar to alignment adopted in the retinal camera of the related art. Step S1003 corresponds to awaiting period for the next step to be performed by the examiner's entry from the tomographic-image pickup button 1203 on the screen or the control switch 804. In this step, the program of the control unit 125 determines that a command to capture a tomographic image is input when the tomographic-image pickup button 1203 serving as the signal input unit of the imaging operation or the control switch 804 is pressed. To adjust a necessary portion of the retina to be imaged, a light-emitting point of the fixation lamp 320 is adjusted as an adjustment to be made on the side of the eye 107, and the tomographic-image pickup area 1202 is adjusted by the button 1204 on the screen or a controller (not shown) provided in the eyeground-image pickup unit 300.

In Step S1004, when the examiner clicks the tomographic-image pickup button 1203 on the screen or presses the control button 804, the control unit 125 receives this input, and causes the XY scanner 408 to scan according to set information. Simultaneously, the control unit 125 opens the shutter 183 so as to apply the measurement light onto the eye 107. In contrast, the quick-return mirror 318 in the eyeground-image pickup unit 300 remains down, and only the infrared light for tomographic imaging is guided to the dichroic mirror 405 for splitting, so that no light is guided to the camera unit 500. Here, the control unit 125 reads interference signals at positions on the eyeground from the line sensor 182 by operating the XY scanner 408. On the other hand, light having multiplexed wavelengths is incident on pixels of the line sensor 182. Wavelengths obtained by subjecting intensity information about the wavelengths to Fourier conversion by the line sensor 182 serve as intensity information about return light at the positions of the eyeground in the depth direction. This is based on the general principle of a spectral domain OCT (SD-OCT). One-dimensional data on a certain point on the eyeground in the depth direction is referred to as A-scan data. In this step, scanning is performed until intensity information about each position is acquired. After the completion of scanning, the shutter 183 is closed and the XY scanner 408 is stopped.

Step S1004 automatically shifts to Step S1005, where a tomographic-image check screen is displayed, as shown in FIG. 5A. A tomographic-image check display 1305 displays tomographic images in the x-direction, which are captured at a certain position in the y-direction (A-scan data are arranged in the x-direction, and referred to as B-scan images), together with the scanning number 1305. Here, only about one-fifth of all B-scan images are displayed. By changing the setting, all B-scan images can be displayed, or conversely, only one-tenth of all B-scan images can be displayed. In this tomographic-image check display 1305, small images are arranged in tiles so as to be checked easily. The displayed B-scan images for checking form tomographic images by thinning A-scan data in the x-direction. For example, while 1024 lines of A-scan data in the x-direction are captured according to the scan setting shown in FIG. 4A, only 256 lines are displayed in this case. By subjecting only 256 lines of data to Fourier conversion and displaying the 256 lines side by side, one check tomographic image is obtained. While operation, such as fixed noise removal, is performed when observation tomographic images are formed in a later step for diagnosis, check images are obtained without performing the above-described operation in this case. This allows the check images to be more quickly displayed, and shortens the time taken for check and shift to the next step. In FIG. 5A, an eyeground-image button 1301 is a signal input unit of the imaging operation. When there is no failure in tomographic imaging, a save button 1303 is clicked to store, in the storage unit 129, the tomographic images, a plurality of pieces of intensity information obtained from the line sensor 182 before the tomographic images are formed, or both of them. At the time of saving, not only a series of tomographic images are stored, but also the infrared-image screen 1201 used in Step S1003 is stored. This allows the tomographic-image pickup area 1202 to be easily checked after imaging. A tomographic-image retake button 1304 serves as a selection input unit. To prevent an eyeground image from being captured without a saving operation, the eyeground-image pickup button 1301 may be displayed after the saving button 1303 is pressed. This step corresponds to a waiting period in which a click of the eyeground imaging button 1301 or the tomographic-image recapturing button 1304 or a press of the control switch 804 is waited for after the check tomographic image is displayed. In this step, the program of the control unit 125 determines that the press of the eyeground-image pickup button 1301 or the control switch 804 corresponds to input of a command to capture an eyeground image, unlike in Step S1003. The examiner checks whether or not tomographic imaging fails halfway because of a blink, involuntary eye movement, or other causes while viewing the tomographic-image check display 1305. For example, when a blink occurs, some B-scan images become seriously darker than the other B-scan images. When involuntary eye movement is large, a portion of the retina to be observed is not included in some B-scan images. On the other hand, when images having a relatively large quantity of A-scan data to be acquired, that is, high-definition tomographic images are three-dimensionally obtained, as in this example, the imaging time increases. As described in Step S1002, a blink is highly likely to occur in the imaging time of about 3.7 seconds, as described in Step S1002. When the images have the above-described defects, the examiner determines that tomographic imaging fails. Here, while the examiner determines whether or not acquisition of tomographic images is successful, the control unit 125 may determine whether or not a dark image is included in obtained B-scan images, and a display may be automatically made to urge the examiner to perform check, for example, an image judged a failure may be surrounded with a red frame.

In Step S1006, when tomographic imaging is successful, the examiner checks the position of the eyeground with the monitor 128. When necessary, the examiner readjusts the position, and then clicks the eyeground-image pickup button 1301 or presses the control button 804. In this case, the control unit 125 shifts the step to the next Step S1007. When tomographic imaging fails and it is necessary to capture a tomographic image again, the tomographic-image retake button 1304 is clicked. At this time, the control unit 125 performs Step S1004 again so as to retake a tomographic image.

In Step S1007, an eyeground image is captured. The stroboscopic tube 314 is caused to emit light, and simultaneously, the quick-return mirror 318 is flipped up. In this state, an eyeground image is captured with the camera unit 500, and is stored in the storage unit 129.

In Step S1008, imaging is finished.

By clicking an "IMAGING RESULT DISPLAY" tab on the screen after a series of image pickup operations are finished, a tomographic-image display screen shown in FIG. 5B is displayed. Reference numeral 1401 denotes a B-scan image serving as one of the obtained tomographic images. By operating a slider 1403 for B-scan selection, a B-scan image 1401 at a desired position is displayed. Reference numeral 1402 denotes an obtained eyeground image, and a tomographic-image pickup area 1405 is also displayed. The eyeground image displayed here is obtained by eyeground imaging, but is different from the infrared image 1201 of the eyeground stored in Step S1005. An image-quality setting slider 1404 for setting the quality of the tomographic image display is used to adjust the brightness and contrast of the image. Broken lines are shown for explanation, and in actuality, are not displayed on the screen. A stop button 1406 is similar to the stop button on the above-described display screen. The tomographic image displayed here is different from the tomographic image displayed for check in Step S1005. Thinning of A-scan data is minimized within the display range, and fixed noise is removed by operation. This allows precise observation of the tomographic image.

As described above, the eyeground imaging apparatus of the first example displays a tomographic image for checking between pickup of a tomographic image and pickup of an eyeground image, and selects between transition to pickup of an eyeground image and retake of a tomographic image. In this case, even if the apparatus simultaneously performs pickup of an eyeground image and pickup of a tomographic image that needs a relatively long imaging time, a tomographic image can be retaken without waiting for recovery of the eye from contraction of the pupil due to a flare of flashlight. Moreover, since the control switch can be operated to capture a tomographic image or to capture an eyeground image in accordance with the state of the screen display, the apparatus can be simplified.

While tomographic imaging is performed by SD-OCT in the first example, it may be performed by time domain OCT (TD-OC) or swept-source OCT (SS-OCT).

Second Example

Preview of Tomographic Image

Next, an eyeground imaging apparatus according to a second example will be described. The second example is different from the first example in a part of a method for capturing a tomographic image and an eyeground image. Since the configuration of the apparatus, configuration of an optical system of the apparatus, and a configuration of a tomographic-image pickup unit are similar to those adopted in the first example, descriptions thereof are omitted, and a method for capturing a tomographic image and an eyeground image will be described.

[Method for Capturing Tomographic Image and Eyeground Image]

Figure 6:
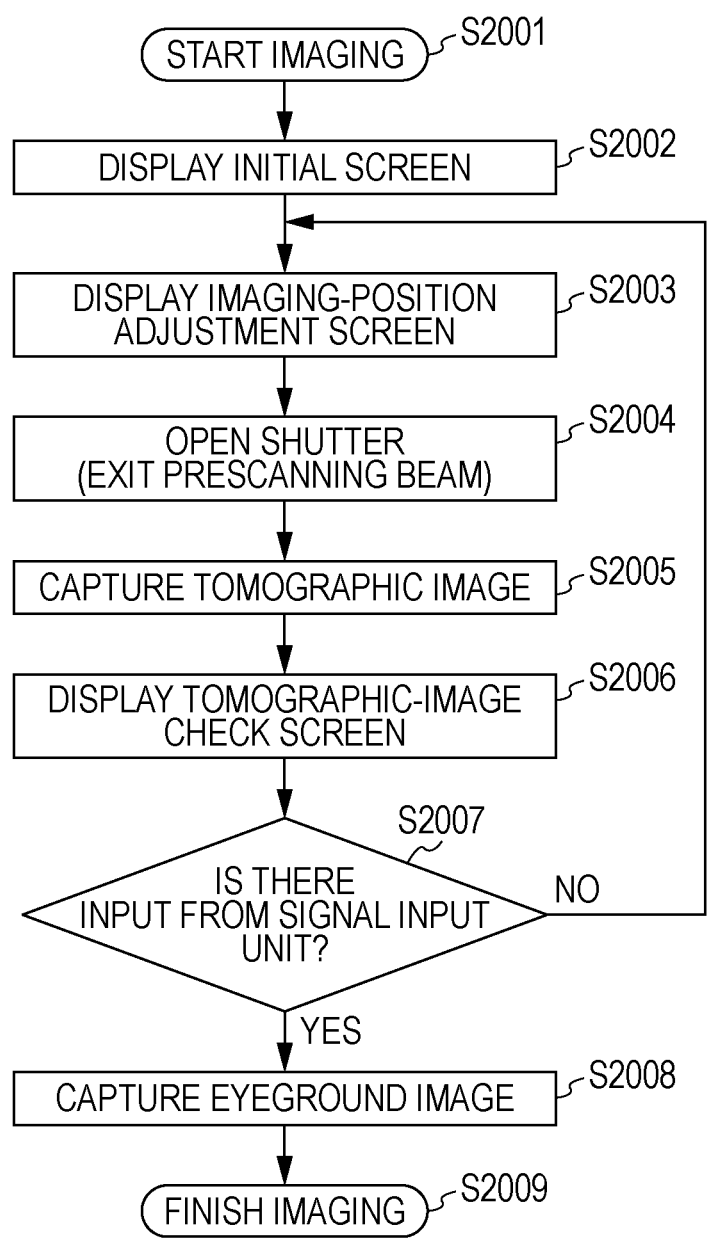
FIG. 6 is a flowchart showing image acquisition in the second example.

An image capturing method using the eyeground imaging apparatus of the second example will be described with reference to FIGS. 4C and 6. The same structures of the apparatus as those of the first example are denoted by the same reference numerals. Steps in an imaging flowchart shown in FIG. 6 will be described in order.

In Step S2001, imaging is started. A control unit 125 executes an imaging program, and displays an imaging screen on a control-unit monitor 128, in a manner similar to Step S1001 of the first example.

In Step S2002, an examination information screen is displayed on the control-unit monitor 128, in a manner similar to Step S1002 of the first example.

In Step S2003, an imaging-position adjustment screen is displayed on the control-unit monitor 128, as shown in FIG. 4C. The display on the control-unit monitor 128 is switched by the examiner's click of an "ALIGNMENT" tab shown in FIG. 4A. An infrared eyeground-image screen 2201 displays a tomographic-image pickup area 2208 superimposed on an image captured by an infrared area sensor 321 shown in FIG. 2A. A button 2204 is used to move the tomographic-image pickup area 2208 up, down, right, and left. A tomographic-image pickup button 2203 is not displayed in Step S2003, but is displayed in the next Step S2004. A stop button 2206 is similar to the stop button adopted in the first example. In this step, the examiner aligns an imaging apparatus 200 and an eye 107 to be examined. Since alignment is performed in a manner similar to that adopted in the first example, a description thereof is omitted. FIG. 4C also illustrates a preview screen 2202 for a tomographic image, a slider 2207 for indicating the gate position, and a signal-level indicator 2205. These portions will be described in the following description of Step S2004. Broken lines are shown for explanation, but are not displayed on an actual screen. In this Step S2003, the imaging program determines that a signal for capturing a tomographic image for a preview (Step S2004) is input when a control switch 804 serving as an input unit for imaging is pressed. Further, a light-emitting position of a fixation lamp 320 is adjusted as adjustment made on the side of the eye 107 to adjust a necessary imaging portion of the retina, and the position of the tomographic-image pickup area 2208 is adjusted with the button 2204 on the screen or a controller (not shown) provided in a main unit 300. The adjustment of the light-emitting position of the fixation lamp 320 and the adjustment of the tomographic-image pickup area 2208 can be made in this step and the next Step S2004.

In Step S2004, when the examiner presses the control switch 804, an XY scanner 408 starts, and simultaneously, a shutter 183 opens to apply measurement light onto the eye 107, so that preview scanning starts to adjust tomographic imaging. Simultaneously, the tomographic-image pickup button 2203 serving as the signal input unit for imaging is displayed on the screen. This preview scanning is performed near a center line 2208a of the tomographic-image pickup area 2208 in the horizontal direction in FIG. 4C, and an obtained B-scan image is displayed on the tomographic-image preview screen 2202. During preview scanning, B-scan images are recaptured at the same position in the y-direction, and are displayed sequentially. The examiner makes adjustments for tomographic imaging while viewing the tomographic-image preview screen 2202. First, gate position adjustment is made with a stage controller (not shown). Gate position adjustment refers to adjustment for the difference in optical path length from reference light by moving an electric stage (117 in FIG. 2B) to which a mirror 114 in FIG. 2B for folding the reference light. That is, gate position adjustment is adjustment for a cross-sectional position of the retina in the vertical direction of the screen. Particularly in tomographic imaging, the brightness becomes the highest at a position where the optical path lengths of the reference light and the object to be measured coincide with each other (this position is referred to as a gate position). Hence, it is necessary that the cross-sectional position of the retina should be located near a position where the optical path length thereof coincides with the optical path length of the reference light. However, if the gate position is set in the cross section of the retina, a mirror image due to Fourier conversion appears on the screen on the principle of SD-OCT. Hence, in order to obtain the best image, the retina position is set to be near the gate position, but not to be in the cross section of the retina. While the examiner adjusts the gate position in this example, the control unit 125 may automatically adjust the gate position on the basis of, for example, the brightness in the screen. The slider 2207 for indicating the gate position indicates where the gate position is located on the examiner side or the subject side, and functions as a guide for movement of the electric stage 117. Further, the signal-level indicator 2205 indicates the ratio of the maximum brightness of the preview B-scan image and the brightness of background noise. As the position of a mark in the signal-level indicator 2205 moves to the right, the brightness of the image increases. With reference to this indicator 2205, the examiner adjusts the focus or finely adjusts the position of the main unit 300 with the joystick 805. This step corresponds to a waiting period for the next step of tomographic imaging to be performed when the examiner makes input from the tomographic-image pickup button 2203 on the screen or the control switch 804. In this step, the program of the control unit 125 determines that a signal for tomographic imaging is input when the tomographic-image pickup button 2203 serving as the input unit for the imaging signal or the control switch 804 is pressed, in a manner similar to Step S1003 of the first example. Moreover, in a manner similar to Step S1003 of the first example, the light-emitting position of the fixation lamp 320 is adjusted as adjustment to be made on the side of the eye 107 in order to adjust the necessary imaging position of the retina, and the tomographic-image pickup area 2208 is adjusted with the button 2204 on the screen or the controller (not shown) provided in the main unit 300.

In Step S2005, when the examiner clicks the tomographic-image pickup button 2203 on the screen or presses the control switch 804, the control unit 125 receives this input, and tomographic images are captured, in a manner similar to that adopted in the first example.

Step S2005 automatically shifts to Step S2006. In Step S2006, a tomographic-image check screen is displayed, in a manner similar to that adopted in the first example. In this step, after a tomographic image for check is displayed, a click of an eyeground-image pickup button 1301 or a tomographic-image retake button 1304 on the screen or a press of the control switch 804 is waited for. In this step, the program of the control unit 125 determines that a signal for capturing an eyeground image is input when the eyeground-image pickup button 1301 serving as the input unit for the image pickup signal or the control switch 804 is pressed, in a manner similar to that adopted in the first example.

In Step S2007, the examiner views the tomographic-image check display, and checks whether or not tomographic imaging fails halfway because of a blink, involuntary eye movement, or other causes. When tomographic imaging is successful, the examiner checks position adjustment with respect to the eyeground on the monitor 128. If readjustment is necessary, it is made, and then, the eyeground-image pickup button 1301 is clicked or the control switch 804 is pressed.

When tomographic imaging fails and it is necessary to retake a tomographic image, the process can be returned to Step S2003 by clicking the "ALIGNMENT" tab serving as the selection input portion in this step. This allows the gate, focus, and position of the main unit to be more finely adjusted in retaking of the tomographic image.

In Step S2008, an eyeground image is captured in a manner similar to that adopted in the first example.

In Step S2009, imaging is finished.

By clicking an "IMAGING RESULT DISPLAY" tab on the screen after imaging is finished, a tomographic-image display screen is displayed, in a manner similar to that adopted in the first example.

If the stop button 2204 is clicked during preview display in Step S2004, or when the screen is changed to another screen by a click of a tab different from the "ALIGNMENT" tab, the shutter 183 is closed to block the measurement light so that the measurement light does not travel toward the subject side. When the "ALIGNMENT" tab is clicked again, the state in Step S2003 is brought about.

As described above, the eyeground imaging apparatus of the second example performs a preview of a tomographic image in imaging adjustment (Step S2003), in addition to the operations performed in the first example. Therewith, the state of the apparatus can be adjusted to improve the quality of a captured tomographic image, for example, when only one B-scan tomographic image is captured. Further, since the process can be returned to the step of imaging adjustment (Step S2003) at the time of retake of a tomographic image, the gate, focus, and position of the main unit can be adjusted more finely. In addition, preview scanning can be started with the control switch, and this simplifies the apparatus and reduces the operation load on the examiner.

Third Example

Adaptor

Next, an eyeground imaging apparatus according to a third example will be described.

The third example is different from the first example in a part of a configuration of the apparatus. In the following, structures similar to those adopted in the first example denoted by the same reference numerals, and descriptions thereof are omitted.

An overall configuration of the eyeground imaging apparatus of the third example will be described with reference to FIGS. 1B and 1C. FIG. 1B is a side view of an eyeground imaging apparatus 200 of the third example. The imaging apparatus 200 includes a tomographic-image pickup unit 100, a retinal-camera main unit 900, an adaptor 400, and a camera unit 500. The retinal-camera main unit 900, the adaptor unit 400, and the camera unit 500 are connected optically. The retinal-camera main unit 900 and the adaptor 400 are held to be movable relative to each other so that rough optical adjustment is possible. Further, the adaptor unit 400 and the tomographic-image pickup unit 100 are optically connected by an optical fiber 148. The adaptor 400 and the tomographic-image pickup unit 100 have a connector 410 and a connector 147, respectively, and therefore, can be attached and detached easily. The eyeground imaging apparatus 200 also includes a personal computer 925 for forming a tomographic image and a control-circuit unit 905. The personal computer 925 and the control-circuit unit 905 are similar to the control unit adopted in the first example. A personal-computer monitor 928 and a storage unit 929, such as a hard disk, may be incorporated in the personal computer 925.

Figure 1C:
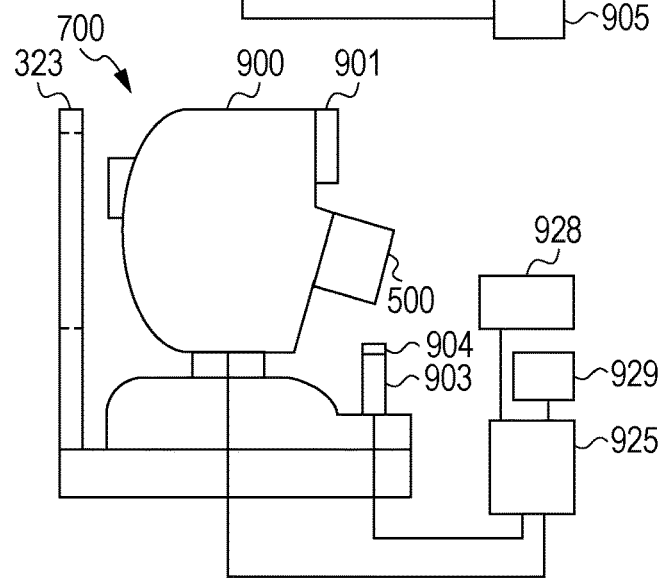
FIG. 1C is a schematic view illustrating the overall configuration of the eyeground imaging apparatus according to the third example.

Alternatively, as shown in FIG. 1C, the retinal-camera main unit 900 and the camera unit 500 can constitute one retinal camera 700. Since the tomographic-image pickup unit 100 is not used in this case, the control circuit unit 905 is also unnecessary. The retinal camera 700 can be changed to the eyeground imaging apparatus by detaching the camera unit 500 from the retinal-camera main unit 900 and attaching the adaptor 400 between the camera unit 500 and the retinal-camera main unit 900.

[Configurations of Optical Systems of Retinal Camera, Adaptor, and Camera Unit]

Figure 7A:
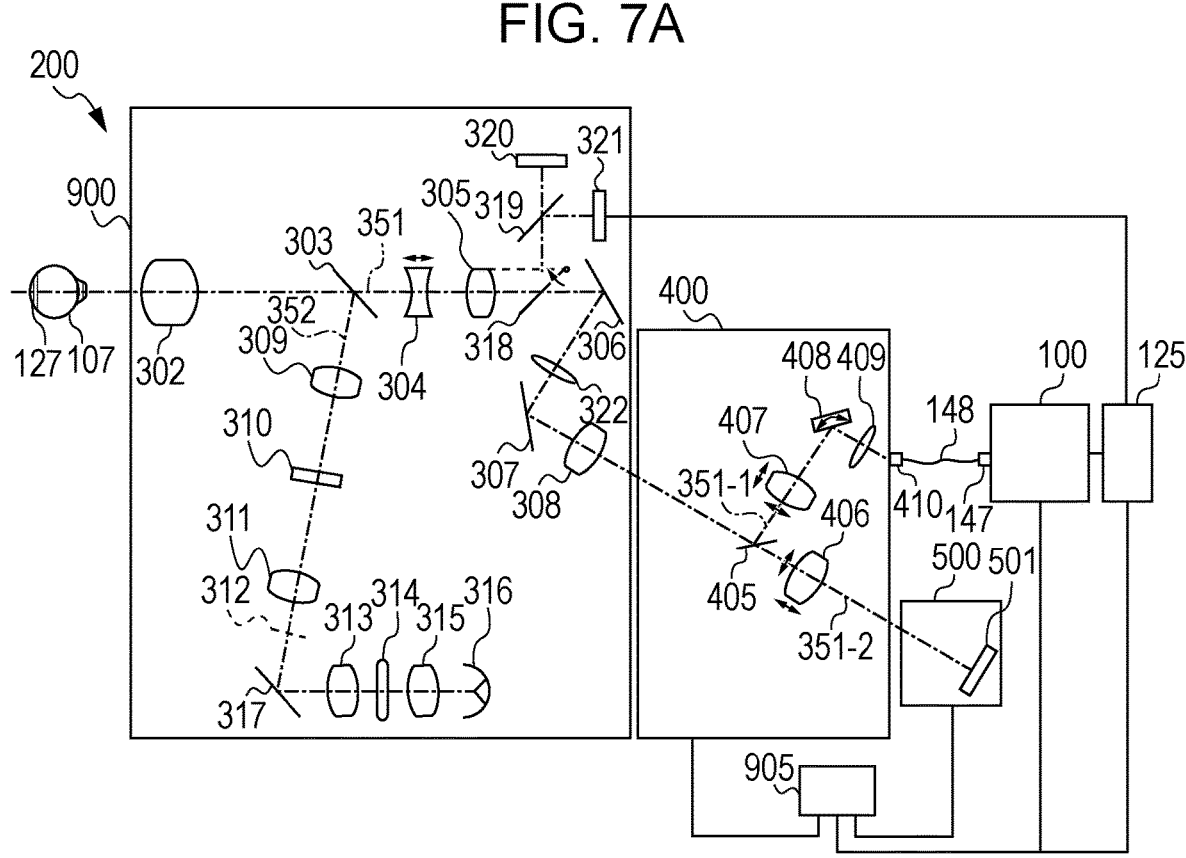
FIG. 7A is a schematic view illustrating a configuration of an optical system of the third example.

The configuration of the optical system of the eyeground imaging apparatus of the third example including the adaptor will be described with reference to FIG. 7A. The same components as those adopted in the first example are denoted by the same reference numerals. In the third example, the main unit of the first example of the first example is divided into the retinal camera unit 900 and the adaptor 400. The adaptor 400 includes a dichroic mirror 405, relay lenses 406 and 407, a collimator lens 409, an XY scanner 408, and the connector 410. An optical system on the eye side including an optical path 351 is entirely included in the retinal-camera unit 900. Since details of the structures are similar to those adopted in the first example, descriptions thereof are omitted. In the retinal camera 700 shown in FIG. 1C, the relay lens 308 in the retinal-camera unit 900 serves to form an eyeground image on an area sensor 501 provided in the camera unit 500.

[Structure of Tomographic-Image Pickup Unit]

Since the structure of the tomographic-image pickup unit 100 is similar to that adopted in the first example, a description thereof is omitted. However, a portion connected to the control unit 125 in the first example is connected to the control-circuit unit 905 in the third example.

[Method for Capturing Tomographic Image and Eyeground Image]

Figure 7B:
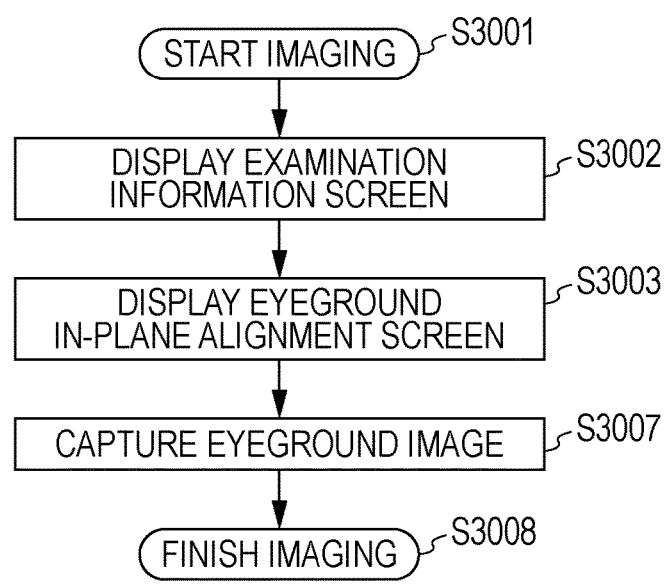
FIG. 7B is a flowchart showing image acquisition in the third example.

First, a method for capturing an eyeground image with the retinal camera 700 shown in FIG. 1C will be described with reference to a flowchart of FIG. 7B.

In Step S3001, imaging starts, a program only for the retinal camera 700 is started on the monitor 928 by the personal computer 925, and an imaging screen is displayed, in a manner similar to Step S1001 of the first example.

In Step S3002, an examination information screen is displayed. While this step is substantially equivalent to Step S3002 of the first example, scanning is not performed in the third example. Hence, information about scanning is not displayed.

In Step S3003, an eyeground in-plane alignment screen is displayed. When the retinal camera is used, an infrared eyeground image for position adjustment is displayed on a monitor 901, and the examiner adjusts the position of the retinal-camera main unit 900 with a joystick 903 and adjusts the focus with a knob (not shown) on the basis of the displayed infrared eyeground image. In this step, the program only for the retinal camera 700 determines to capture an eyeground image when a signal for imaging is input from a control switch 904 serving as an input unit for the imaging signal. In response to the signal, the process proceeds to Step S3004.

In Step S3004, an eyeground image is captured, in a manner similar to Step S1007 of the first example. Data on the captured eyeground image is displayed on the monitor 928 via the retinal-camera main unit 900, and is stored in the storage unit 929.

In Step S3005, imaging is finished.

A method for capturing a tomographic image and an eyeground image with the imaging apparatus 200 is similar to that adopted in the first and second examples, and therefore, a description thereof is omitted.

When the retinal camera 700 is changed to the eyeground imaging apparatus 200, the tomographic-image pickup unit 100, the adaptor 400, the camera unit 500, and the retinal-camera main unit 900 are connected to the personal computer 925 via the control-circuit unit 905. A light source, a shutter, a line sensor, and an XY scanner, which are controlled objects specific to tomographic imaging, have a driver and so on in the control-circuit unit 905, and can be controlled with the personal computer 925 by connecting the control-circuit unit 905 between the adaptor 400 and the personal computer 925. Further, the control switch 904 provided in the retinal-camera main unit 900 and the camera unit 500 are also connected to the control-circuit unit 905, and can thereby be controlled as the eyeground imaging apparatus 200, unlike the retinal camera 700. This can respond to different functions of the signal input unit 904 corresponding to the steps in a manner similar to that adopted in the first and second examples. For example, while preview scanning is started when the control switch 904 is pressed in Step S2004 of FIG. 6, control specific to the eyeground imaging apparatus 200 can be performed in this case, for example, pickup of an eyeground image with the camera unit 500 is not performed even when the control switch 904 is pressed.

Accordingly, in the third example, the retinal camera can be easily changed to the eyeground imaging apparatus capable of capturing a tomographic image. Moreover, the control switch is commonly used in the retinal camera and the eyeground imaging apparatus. This reduces the number of components, and allows both the retinal camera and the eyeground imaging apparatus to be used without substantially changing usability of the examiner and without giving any feeling of discomfort to the examiner.

Other Embodiments

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment (s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An imaging apparatus comprising:
a scanning unit configured to perform scanning with measurement light on a subject's eye;
a tomographic-image obtaining unit configured to obtain a first tomographic image of the subject's eye using combined light obtained by combining return light returned from the subject's eye irradiated with the measurement light via the scanning unit with reference light corresponding to the measurement light, and to obtain a second tomographic image of the subject's eye in response to an instruction to obtain the second tomographic image; and
a control unit configured to (a) cause a display unit to display the first tomographic image and a first display information about image quality of the first tomographic image, (b) to cause, after the instruction is performed in a state that the first tomographic image and the first display information are displayed on the display unit, the display unit to shift a layout on a screen of the display unit from a first layout for displaying the first tomographic image and the first display information to a second layout for displaying the second tomographic image obtained in response to the instruction, second display information about image quality of the second tomographic image, and third display information for instructing re-obtainment of the second tomographic image of the subject's eye, and (c) to cause, in response to an instruction for the third display information for instructing the re-obtainment, the display unit to back the layout on the screen of the display unit from the second layout to the first layout.

2. The imaging apparatus according to claim 1, wherein the control unit is configured to cause the display unit to display, as the second display information, a display information indicating a result of determination of whether the second tomographic image is adequate.

3. The imaging apparatus according to claim 1, wherein the control unit is configured to cause the display unit to display, as the second display information, a display information for displaying the second tomographic image with a frame thereof being emphasized.

4. The imaging apparatus according to claim 1, wherein the control unit is configured to cause the display unit to display, as the first display information, a display information for indicating a ratio of brightness of background noise and maximum brightness of the first tomographic image.

5. The imaging apparatus according to claim 1, wherein the control unit is configured to cause the display unit to display, as the first display information, an indicator indicating brightness of the first tomographic image.

6. The imaging apparatus according to claim 1, wherein the control unit is configured to cause the display unit to display the first tomographic image and the first display information side by side on a same screen of the display unit, and to cause, after the first tomographic image and the first display information are displayed side by side on the same screen of the display unit, the display unit to display the second tomographic image obtained in response to the instruction, the second display information, a save button for instructing a save of the second tomographic image obtained in response to the instruction, and the third display information for instructing the re-obtainment side by side on a same screen of the display unit.

7. The imaging apparatus according to claim 1, wherein the tomographic-image obtaining unit is configured to obtain a plurality of the first tomographic images in succession, and
wherein the control unit is configured to cause the display unit to sequentially display the plurality of the first tomographic images having been consecutively obtained and a first display information about image quality, for each of the plurality of the first tomographic images having been consecutively obtained.

8. An imaging apparatus comprising:
a scanning unit configured to perform scanning with measurement light on a subject's eye;
a tomographic-image obtaining unit configured to obtain a tomographic image of the subject's eye using combined light obtained by combining return light returned from the subject's eye irradiated with the measurement light via the scanning unit with reference light corresponding to the measurement light; and
a control unit configured (a) to cause, after an instruction to obtain the tomographic image is performed, a display unit to shift a layout on a screen of the display unit from a first layout to a second layout for displaying the tomographic image obtained in response to the instruction and display information for instructing re-obtainment of the tomographic image of the subject's eye, and (b) to cause, in response to an instruction for the display information instructing the re-obtainment, the display unit to back the layout on the screen of the display unit from the second layout to the first layout, the first layout being for displaying display information for instructing an adjustment of a difference between an optical length of the measurement light and an optical length of the reference light.

9. The imaging apparatus according to claim 8, wherein the control unit is configured to cause the display unit to display, on at least one of the first layout and the second layout display information for indicating a result of determination of whether the tomographic image is adequate.

10. The imaging apparatus according to claim 8, wherein the control unit is configured to cause the display unit to display, on at least one of the first layout and the second layout display information for displaying the tomographic image with a frame thereof being emphasized.

11. A control apparatus comprising:
a tomographic-image obtaining unit configured to obtain a first tomographic image of a subject's eye using combined light obtained by combining return light returned from the subject's eye irradiated with measurement light with reference light corresponding to the measurement light, and to obtain a second tomographic image of the subject's eye in response to an instruction to obtain the second tomographic image; and
a display control unit configured (a) to cause a display unit to display the first tomographic image and a first display information about image quality of the first tomographic image, and (b) to cause, after the instruction is performed in a state that the first tomographic image and the first display information are displayed on the display unit, the display unit to shift a layout on a screen of the display unit from a first layout for displaying the first tomographic image and the first display information to a second layout for displaying the second tomographic image obtained in response to the instruction, second display information about image quality of the second tomographic image, and third display information for instructing re-obtainment of the second tomographic image of the subject's eye, and (c) to cause, in response to an instruction for the display information for instructing the re-obtainment, the display unit to back the layout on the screen of the display unit from the second layout to the first layout.

12. The control apparatus according to claim 11, wherein the display control unit is configured to cause the display unit to display, as the second display information, display information for displaying the second tomographic image with a frame thereof being emphasized.

13. The control apparatus according to claim 11, wherein the display control unit is configured to cause the display unit to display, as the first display information, a display information for indicating a ratio of brightness of background noise and maximum brightness of the first tomographic image.

14. The control apparatus according to claim 11, wherein the display control unit is configured to cause the display unit to display, as the first display information, an indicator indicating brightness of the first tomographic image.

15. The control apparatus according to claim 11, wherein the display control unit is configured to cause the display unit to display the first tomographic image and the first display information side by side on a same screen of the display unit, and to cause, after the first tomographic image and the first display information are displayed side by side on the same screen of the display unit, the display unit to display the second tomographic image obtained in response to the instruction, the second display information, a save button for instructing a save of the second tomographic image obtained in response to the instruction, and the third display information for instructing the re-obtainment side by side on a same screen of the display unit.

16. The control apparatus according to claim 11, wherein the display control unit is configured to cause the display unit to display, as the second display information, display information for indicating a result of determination of whether the second tomographic image is adequate.

17. The control apparatus according to claim 11,
wherein the tomographic-image obtaining unit is configured to obtain a plurality of the first tomographic images in succession, and
wherein the display control unit is configured to cause the display unit to sequentially display each of the plurality of the first tomographic images having been consecutively obtained and a first display information about image quality for each of the plurality of the first tomographic images having been consecutively obtained.

18. The control apparatus according to claim 11, wherein the control apparatus controls an imaging apparatus including a scanning unit configured to perform scanning with measurement light in two directions intersecting with each other on a subject's eye.

19. The control apparatus according to claim 18, wherein the control apparatus controls the scanning unit to thereby enable the second tomographic image of the subject's eye to be re-obtained.

20. A control apparatus comprising:
a tomographic-image obtaining unit configured to obtain a tomographic image of a subject's eye, obtain the tomographic image using combined light obtained by combining return light returned from the subject's eye irradiated with measurement light with reference light corresponding to the measurement light; and
a display control unit configured (a) to cause, after an instruction to obtain the tomographic image is performed, a display unit to shift a layout on a screen of the display unit from a first layout to a second layout for displaying the tomographic image obtained in response to the instruction and display information for instructing re-obtainment of a tomographic image of the subject's eye, and (b) to cause, in response to an instruction for the display information for instructing the re-obtainment, the display unit to back the layout on the screen of the display unit from the second layout to the first layout, the first layout being for displaying display information for instructing an adjustment of a difference between an optical length of the measurement light and an optical length of the reference light.

21. The control apparatus according to claim 20, wherein the control apparatus controls an imaging apparatus including a scanning unit configured to perform scanning with measurement light in two directions intersecting with each other on a subject's eye.

22. The control apparatus according to claim 21, wherein the control apparatus controls the scanning unit to thereby enable the second tomographic image of the subject's eye to be re-obtained.

23. The control apparatus according to claim 20, wherein the display control unit is configured to cause the display unit to display, on at least one of the first layout and the second layout, display information for indicating a result of determination of whether the tomographic image is adequate.

24. The control apparatus according to claim 20, wherein the display control unit is configured to cause the display unit to display, on at least one of the first layout and the second layout, display information for displaying the tomographic image with a frame thereof being emphasized.

25. A control method comprising:
obtaining a first tomographic image of a subject's eye using combined light obtained by combining return light returned from the subject's eye irradiated with measurement light via a scanning unit configured to perform scanning with the measurement light on the subject's eye with reference light corresponding to the measurement light, and obtaining a second tomographic image of the subject's eye in response to an instruction to obtain the second tomographic image;
controlling a display unit to display the first tomographic image and first display information about image quality of the first tomographic image,
controlling, after the instruction is performed in a state that the first tomographic image and the first display information are displayed on the display unit, the display unit to shift a layout on a screen of the display unit from a first layout for displaying the first tomographic image and the first display information to a second layout for displaying the second tomographic image obtained in response to the instruction a second display information about image quality of the second tomographic image, and third display information for instructing re-obtainment of the second tomographic image of the subject's eye, and
controlling, in response to an instruction for the third display information for instructing the re-obtainment, the display unit to back the layout on the screen of the display unit from the second layout to the first layout.

26. A non-transitory computer-readable storage medium for storing a program that causes a computer to perform the control method according to claim 25.

27. A control method comprising:
obtaining a tomographic image of a subject's eye using combined light obtained by combining return light returned from the subject's eye irradiated with measurement light via a scanning unit configured to perform scanning with the measurement light on the subject's eye with reference light corresponding to the measurement light;
controlling, after an instruction to obtain the tomographic image is performed, a display unit to shift a layout on a screen of the display unit from a first layout to a second layout for displaying the tomographic image obtained in response to the instruction and display information for instructing re-obtainment of the tomographic image of the subject's eye; and
controlling, in response to an instruction for the display information for instructing the re-obtainment, the display unit to back the layout on the screen of the display unit from the second layout to the first layout, the first layout being for displaying display information for instructing an adjustment of a difference between an optical length of the measurement light and an optical length of the reference light.

28. A non-transitory computer-readable storage medium for storing a program that causes a computer to perform the control method according to claim 27.

29. A control method comprising:
obtaining a first tomographic image of a subject's eye using combined light obtained by combining return light returned from the subject's eye irradiated with measurement light with reference light corresponding to the measurement light, and obtaining a second tomographic image of the subject's eye in response to an instruction to obtain the second tomographic image;
controlling a display unit to display the first tomographic image and a first display information about image quality of the first tomographic image;
controlling, after the instruction is performed in a state that the first tomographic image and the first display information are displayed on the display unit, the display unit shift a layout on a screen of the display unit from a first layout for displaying the first tomographic image and the first display information to a second layout for displaying the second tomographic image obtained in response to the instruction, a second display information about image quality of the second tomographic image, and third display information for selecting re-obtainment of the second tomographic image of the subject's eye, and
controlling, in response to an instruction for the third display information for instructing the re-obtainment, the display unit to back the layout on the screen of the display unit from the second layout to the first layout.

30. A non-transitory computer-readable storage medium for storing a program that causes a computer to perform the control method according to claim 29.

31. A control method comprising:
obtaining a tomographic image of a subject's eye using combined light obtained by combining return light returned from the subject's eye irradiated with measurement light with reference light corresponding to the measurement light;
controlling, after an instruction to obtain the tomographic image is performed, a display unit to shift a layout on a screen of the display unit from a first layout to a second layout for displaying the tomographic image obtained in response to the instruction and display information for instructing re-obtainment of the tomographic image of the subject's eye; and
controlling, in response to an instruction for the display information for instructing the re-obtainment, the display unit to back the layout on the screen of the display unit from the second layout to the first layout, the first layout being for displaying display information for instructing an adjustment of a difference between an optical length of the measurement light and an optical length of the reference light.

32. A non-transitory computer-readable storage medium for storing a program that causes a computer to perform the control method according to claim 31.

33. The imaging apparatus according to claim 1, wherein the control unit is configured to control the scanning unit so that the second tomographic image of the subject's eye is re-obtained in a case where re-obtainment of the second tomographic image of the subject's eye is instructed.

34. The imaging apparatus according to claim 8, wherein the control unit is configured to control the scanning unit so that a tomographic image of the subject's eye is re-obtained in a case where re-obtainment of the tomographic image of the subject's eye is instructed.

35. The imaging apparatus according to claim 1, wherein the control unit is configured to cause the display unit to shift a screen of the display unit in response to instruction for one of tabs displayed on the display unit.

36. The imaging apparatus according to claim 8, wherein the control unit is configured to cause the display unit to shift a screen of the display unit in response to instruction for one of tabs displayed on the display unit.

37. The control apparatus according to claim 11, wherein the display control unit is configured to cause the display unit to shift a screen of the display unit in response to instruction for one of tabs displayed on the display unit.

38. The control apparatus according to claim 20, wherein the display control unit is configured to cause the display unit to shift a screen of the display unit in response to instruction for one of tabs displayed on the display unit.

39. The imaging apparatus according to claim 8, wherein the control unit is configured to cause the display unit to display the tomographic image obtained in response to the instruction, display information about image quality of the tomographic image, the display information for instructing the re-obtainment, and a save button for save the tomographic image obtained in response to the instruction side by side on a same screen of the display unit.

40. The control apparatus according to claim 20, wherein the display control unit is configured to cause the display unit to display the tomographic image obtained in response to the instruction, display information about image quality of the tomographic image, the display information for instructing the re-obtainment, and a save button for save the tomographic image obtained in response to the instruction side by side on a same screen of the display unit.

41. The imaging apparatus according to claim 1, wherein the control unit is configured to cause, using the first layout, the display unit to display the first tomographic image, the first display information, and a display information for instructing an adjustment of a different between an optical length of the measurement light and an optical length of the reference light on a same screen of the display unit.

42. The control apparatus according to claim 11, wherein the display control unit is configured to cause, using the first layout, the display unit to display the first tomographic image, the first display information, and display information for instructing an adjustment of a different between an optical length of the measurement light and an optical length of the reference light on a same screen of the display unit.

43. The imaging apparatus according to claim 8, wherein the control unit is configured to cause, using the first layout, the display unit to display the tomographic image before the instruction, display information about image quality of the tomographic image before the instruction, and the display information for instructing the adjustment on a same screen of the display unit.

44. The control apparatus according to claim 20, wherein the display control unit is configured to cause, using the first layout, the display unit to display the tomographic image before the instruction, display information about image quality of the tomographic image before the instruction, and the display information for instructing the adjustment on a same screen of the display unit.

45. The imaging apparatus according to claim 41, further comprising a changing unit configured to change the different as a gate position, wherein the control unit is configured to cause, using the first layout, the display unit to display the first tomographic image and a slider for instructing the adjustment side by side on the same screen of the display unit, and to control the changing unit using an instruction from a user to the slider.

46. The control apparatus according to claim 42, wherein the display control unit is configured to cause, using the first layout, the display unit to display the first tomographic image and a slider for instructing the adjustment side by side on the same screen of the display unit, and to control a changing unit using an instruction from a user to the slider, the changing unit is configured to change the different as a gate position.

47. The imaging apparatus according to claim 43, further comprising a changing unit configured to change the different as a gate position, wherein the control unit is configured to cause, using the first layout, the display unit to display the tomographic image before the instruction and a slider for instructing the adjustment side by side on the same screen of the display unit, and to control the changing unit using an instruction from a user to the slider.

48. The control apparatus according to claim 44, wherein the display control unit is configured to cause, using the first layout, the display unit to display the tomographic image before the instruction and a slider for instructing the adjustment side by side on the same screen of the display unit, and to control a changing unit using an instruction from a user to the slider, the changing unit is configured to change the different as a gate position.

* * * * *